US009295545B2

(12) United States Patent
Cumming

(10) Patent No.: US 9,295,545 B2
(45) Date of Patent: *Mar. 29, 2016

(54) INTRAOCULAR LENS

(71) Applicant: James Stuart Cumming, Laguna Beach, CA (US)

(72) Inventor: James Stuart Cumming, Laguna Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/035,821

(22) Filed: Sep. 24, 2013

(65) Prior Publication Data

US 2014/0094909 A1    Apr. 3, 2014

Related U.S. Application Data

(63) Continuation-in-part of application No. 13/910,076, filed on Jun. 4, 2013.

(60) Provisional application No. 61/689,394, filed on Jun. 5, 2012.

(51) Int. Cl.
*A61F 2/16* (2006.01)

(52) U.S. Cl.
CPC ............ *A61F 2/1629* (2013.01); *A61F 2/1624* (2013.01); *A61F 2/1635* (2013.01); *A61F 2002/1682* (2015.04)

(58) Field of Classification Search
CPC ... A61F 2/1613; A61F 2/1624; A61F 2/1629; A61F 2/1635; A61F 2/1637; A61F 2/1648; A61F 2002/1681; A61F 2002/1689; A61F 2002/1697; A61F 2002/1682
See application file for complete search history.

(56) References Cited

U.S. PATENT DOCUMENTS

| | | |
|---|---|---|
| 2,834,023 A | 5/1958 | Lieb Wolfgang |
| 4,073,014 A | 2/1978 | Poler |
| 4,118,808 A | 10/1978 | Poler |
| 4,122,556 A | 10/1978 | Poler |
| 4,159,546 A | 7/1979 | Shearing |
| 4,168,547 A | 9/1979 | Konstantinov et al. |
| 4,173,798 A | 11/1979 | Welsh |
| 4,174,543 A | 11/1979 | Kelman |
| 4,206,518 A | 6/1980 | Jardon et al. |
| 4,244,060 A | 1/1981 | Hoffer |
| 4,254,509 A | 3/1981 | Tennant |
| 4,277,851 A | 7/1981 | Choyce et al |
| 4,298,995 A | 11/1981 | Poler |
| 4,304,012 A | 12/1981 | Richard |
| 4,409,690 A | 10/1983 | Gess |
| 4,409,691 A | 10/1983 | Levy |

(Continued)

FOREIGN PATENT DOCUMENTS

| | | |
|---|---|---|
| CA | 2110184 A1 | 12/1992 |
| CH | 681687 | 5/1993 |

(Continued)

OTHER PUBLICATIONS

Dykstra, M., et al. Biological Electron Microscopy: Theory, Techniques, and Troubleshooting, 2003, p. 81.
Final Office Action for U.S. Appl. No. 13/017,189 dated Jul. 18, 2014 in 10 pages.
Final Office Action for U.S. Appl. No. 13/017,189 dated Jan. 13, 2015 in 20 pages.
Final Office Action for U.S. Appl. No. 13/092,359 dated Mar. 5, 2013 in 11 pages.

(Continued)

*Primary Examiner* — Howie Matthews
(74) *Attorney, Agent, or Firm* — Knobbe Martens Olson & Bear LLP

(57) ABSTRACT

An intraocular lens comprising a lens optic coupled to at least one haptic and at least one deformable connecting bar positioned between the lens optic and the at least one haptic.

20 Claims, 1 Drawing Sheet

(56) References Cited

U.S. PATENT DOCUMENTS

| | | |
|---|---|---|
| 4,424,597 A | 1/1984 | Schlegel |
| 4,441,217 A | 4/1984 | Cozean, Jr. |
| 4,477,931 A | 10/1984 | Kelman |
| 4,573,998 A | 3/1986 | Mazzocco |
| 4,585,457 A | 4/1986 | Kalb |
| 4,605,411 A | 8/1986 | Fedorov et al. |
| 4,629,462 A | 12/1986 | Feaster |
| 4,648,878 A | 3/1987 | Kelman |
| 4,664,665 A | 5/1987 | Reuss et al. |
| 4,664,666 A | 5/1987 | Barrett |
| 4,673,406 A | 6/1987 | Schlegel |
| 4,681,102 A | 7/1987 | Bartell |
| 4,704,123 A | 11/1987 | Smith |
| 4,710,195 A | 12/1987 | Glovinazzo |
| 4,718,904 A | 1/1988 | Thornton |
| 4,724,522 A | 2/1988 | Belgorod |
| 4,737,322 A | 4/1988 | Bruns et al. |
| 4,738,680 A | 4/1988 | Herman |
| 4,743,254 A | 5/1988 | Davenport |
| 4,753,655 A | 6/1988 | Hecht |
| 4,759,761 A | 7/1988 | Portnoy |
| 4,763,650 A | 8/1988 | Hauser |
| 4,765,329 A | 8/1988 | Cumming et al. |
| 4,769,033 A | 9/1988 | Nordan |
| 4,769,035 A | 9/1988 | Kelman |
| 4,772,283 A | 9/1988 | White |
| 4,778,463 A | 10/1988 | Hetland |
| 4,781,719 A | 11/1988 | Kelman |
| 4,790,847 A | 12/1988 | Woods |
| 4,793,344 A | 12/1988 | Cumming et al. |
| 4,813,955 A | 3/1989 | Achatz et al. |
| 4,816,030 A | 3/1989 | Robinson |
| 4,840,627 A | 6/1989 | Blumenthal |
| 4,842,599 A | 6/1989 | Bronstein |
| 4,842,601 A | 6/1989 | Smith |
| 4,846,833 A | 7/1989 | Cumming |
| 4,862,885 A | 9/1989 | Cumming |
| 4,865,601 A | 9/1989 | Caldwell et al. |
| 4,868,251 A | 9/1989 | Reich et al. |
| 4,880,427 A | 11/1989 | Anis |
| 4,888,012 A | 12/1989 | Horn et al. |
| 4,892,543 A | 1/1990 | Turley |
| 4,919,130 A | 4/1990 | Stoy et al. |
| 4,932,966 A | 6/1990 | Christie et al. |
| 4,932,968 A | 6/1990 | Caldwell et al. |
| 4,932,970 A | 6/1990 | Portney |
| 4,936,850 A | 6/1990 | Barrett |
| 4,963,148 A | 10/1990 | Sulc et al. |
| 4,969,897 A | 11/1990 | Kalb |
| 4,976,716 A | 12/1990 | Cumming |
| 4,978,354 A | 12/1990 | Van Gent |
| 4,994,082 A | 2/1991 | Richards et al. |
| 5,047,051 A | 9/1991 | Cumming |
| 5,066,297 A | 11/1991 | Cumming |
| 5,078,742 A | 1/1992 | Dahan |
| 5,089,022 A | 2/1992 | Koester et al. |
| 5,139,518 A | 8/1992 | White |
| 5,141,507 A | 8/1992 | Paraekh |
| 5,152,788 A | 10/1992 | Isaacson et al. |
| 5,152,789 A | 10/1992 | Willis |
| 5,171,319 A | 12/1992 | Keates et al. |
| 5,171,320 A | 12/1992 | Nishi |
| 5,180,390 A | 1/1993 | Drews |
| 5,217,490 A | 6/1993 | Sayano et al. |
| 5,275,604 A | 1/1994 | Rheinish et al. |
| 5,275,623 A | 1/1994 | Sarfarazi |
| 5,275,624 A | 1/1994 | Hara et al. |
| 5,290,310 A | 3/1994 | Makower et al. |
| 5,304,182 A | 4/1994 | Rheinish et al. |
| 5,324,306 A | 6/1994 | Makower et al. |
| 5,326,347 A | 7/1994 | Cumming |
| 5,366,502 A | 11/1994 | Patel |
| 5,376,115 A | 12/1994 | Jansen |
| 5,425,734 A | 6/1995 | Blake |
| 5,443,506 A | 8/1995 | Garabet |
| 5,474,562 A | 12/1995 | Orchowski et al. |
| 5,476,514 A | 12/1995 | Cumming |
| 5,489,302 A | 2/1996 | Skottun |
| 5,496,366 A | 3/1996 | Cumming |
| 5,522,891 A | 6/1996 | Klaas |
| 5,562,731 A | 10/1996 | Cumming |
| 5,578,042 A | 11/1996 | Cumming |
| 5,578,078 A | 11/1996 | Nakajima et al. |
| 5,607,472 A | 3/1997 | Thompson |
| 5,611,968 A | 3/1997 | Grisoni et al. |
| 5,647,865 A | 7/1997 | Swinger |
| 5,674,282 A | 10/1997 | Cumming |
| 5,686,414 A | 11/1997 | Scannon |
| 5,699,142 A | 12/1997 | Lee et al. |
| 5,716,403 A | 2/1998 | Tran et al. |
| 5,800,532 A | 9/1998 | Lieberman |
| 5,837,156 A | 11/1998 | Cumming |
| 5,843,187 A | 12/1998 | Bayers |
| 5,873,879 A | 2/1999 | Figueroa et al. |
| 5,919,230 A | 7/1999 | Sambursky |
| 5,944,725 A | 8/1999 | Cicenas et al. |
| 5,968,094 A | 10/1999 | Werblin et al. |
| 5,984,914 A | 11/1999 | Cumming |
| 6,007,579 A | 12/1999 | Lipshitz et al. |
| 6,013,101 A | 1/2000 | Israel |
| 6,015,435 A | 1/2000 | Valunin et al. |
| 6,027,531 A | 2/2000 | Tassignon |
| 6,051,024 A | 4/2000 | Cumming |
| 6,066,171 A | 5/2000 | Lipshitz et al. |
| 6,066,172 A | 5/2000 | Huo et al. |
| 6,113,633 A | 9/2000 | Portney |
| 6,129,760 A | 10/2000 | Fedorov et al. |
| 6,161,544 A | 12/2000 | DeVore |
| 6,164,282 A | 12/2000 | Gwon et al. |
| 6,176,878 B1 | 1/2001 | Gwon et al. |
| 6,179,870 B1 | 1/2001 | Sourdille et al. |
| 6,193,750 B1 | 2/2001 | Cumming |
| 6,197,058 B1 | 3/2001 | Portney |
| 6,197,059 B1 | 3/2001 | Cumming |
| 6,217,612 B1 | 4/2001 | Woods |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,387,126 B1 | 5/2002 | Cumming |
| 6,391,056 B2 | 5/2002 | Cumming |
| 6,406,494 B1 | 6/2002 | Laguette et al. |
| 6,409,763 B1 | 6/2002 | Brady |
| 6,413,276 B1 | 7/2002 | Werblin |
| 6,419,697 B1 | 7/2002 | Kelman |
| 6,423,094 B1 | 7/2002 | Sarfarazi |
| 6,443,985 B1 | 9/2002 | Woods |
| 6,451,056 B1 | 9/2002 | Cumming |
| 6,461,384 B1 | 10/2002 | Hoffmann et al. |
| 6,488,708 B2 | 12/2002 | Sarfarazi |
| 6,494,911 B2 | 12/2002 | Cumming |
| 6,497,708 B1 | 12/2002 | Cumming |
| 6,503,275 B1 | 1/2003 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,540,353 B1 | 4/2003 | Dunn |
| 6,558,420 B2 | 5/2003 | Green |
| 6,613,343 B2 | 9/2003 | Dillingham et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,660,035 B1 | 12/2003 | Lang et al. |
| 6,660,036 B2 | 12/2003 | Cumming |
| 6,685,741 B2 | 2/2004 | Landreville et al. |
| 6,695,881 B2 | 2/2004 | Peng et al. |
| 6,749,634 B2 | 6/2004 | Hanna |
| 6,767,363 B1 | 7/2004 | Bandhauer et al. |
| 6,849,091 B1 | 2/2005 | Cumming |
| 6,858,040 B2 | 2/2005 | Nguyen et al. |
| 6,881,225 B2 | 4/2005 | Okada |
| 6,884,263 B2 | 4/2005 | Valyunin |

(56) References Cited

U.S. PATENT DOCUMENTS

| | | |
|---|---|---|
| 6,921,416 B2 | 7/2005 | Khoury |
| 6,926,736 B2 | 8/2005 | Peng |
| 6,932,839 B1 | 8/2005 | Kamerling et al. |
| 6,969,403 B2 | 11/2005 | Peng |
| 6,972,033 B2 | 12/2005 | McNicholas |
| 7,018,409 B2 | 3/2006 | Glick |
| 7,025,783 B2 | 4/2006 | Brady |
| 7,037,338 B2 | 5/2006 | Nagamoto |
| 7,048,760 B2 | 5/2006 | Cumming |
| 7,097,660 B2 | 8/2006 | Portney |
| 7,125,422 B2 | 10/2006 | Woods et al. |
| 7,150,759 B2 | 12/2006 | Paul et al. |
| 7,150,760 B2 | 12/2006 | Zhang |
| 7,229,475 B2 | 6/2007 | Glazier |
| 7,229,476 B2 | 6/2007 | Azar |
| 7,300,464 B2 | 11/2007 | Tran |
| 7,326,246 B2 | 2/2008 | Brady |
| 7,341,599 B1 | 3/2008 | Peyman |
| 7,435,258 B2 | 10/2008 | Blake |
| 7,435,259 B2 | 10/2008 | Cumming |
| 7,553,327 B2 | 6/2009 | Cumming |
| 7,662,180 B2 | 2/2010 | Paul et al. |
| 7,763,070 B2 | 7/2010 | Cumming |
| 7,837,730 B2 | 11/2010 | Cumming |
| 7,981,155 B2 | 7/2011 | Cumming |
| 7,985,253 B2 | 7/2011 | Cumming |
| 8,038,711 B2 | 10/2011 | Clarke |
| 8,080,056 B2 | 12/2011 | Cumming |
| 8,100,965 B2 | 1/2012 | Cumming et al. |
| 8,109,998 B2 | 2/2012 | Cumming |
| 8,163,015 B2 | 4/2012 | Cumming |
| 8,216,308 B2 | 7/2012 | Blake et al. |
| 8,388,608 B1 | 3/2013 | Kaluzna |
| 8,523,942 B2 | 9/2013 | Cumming |
| 8,734,512 B2 | 5/2014 | Cumming |
| 8,764,823 B2 | 7/2014 | Cumming |
| 9,034,036 B2 | 5/2015 | Cumming |
| 2001/0001836 A1 | 5/2001 | Cumming |
| 2002/0120329 A1 | 8/2002 | Lang et al. |
| 2002/0138140 A1 | 9/2002 | Hanna |
| 2003/0060881 A1 | 3/2003 | Glick et al. |
| 2003/0078658 A1 | 4/2003 | Zadno-Azizi |
| 2003/0097177 A1 | 5/2003 | Tran |
| 2003/0109925 A1 | 6/2003 | Ghazizadeh et al. |
| 2003/0135272 A1 | 7/2003 | Brady et al. |
| 2003/0142269 A1 | 7/2003 | Cumming |
| 2003/0171808 A1 | 9/2003 | Phillips |
| 2003/0171809 A1 | 9/2003 | Phillips |
| 2003/0187505 A1 | 10/2003 | Liao |
| 2003/0199977 A1 | 10/2003 | Cumming |
| 2003/0204257 A1 | 10/2003 | Southard |
| 2004/0002757 A1 | 1/2004 | Lai et al. |
| 2004/0015236 A1 | 1/2004 | Sarfarazi |
| 2004/0082993 A1 | 4/2004 | Woods |
| 2004/0082994 A1 | 4/2004 | Woods et al. |
| 2004/0111152 A1 | 6/2004 | Kelman |
| 2004/0148023 A1 | 7/2004 | Shu |
| 2004/0215207 A1 | 10/2004 | Cumming |
| 2004/0215340 A1 | 10/2004 | Messner et al. |
| 2004/0220666 A1 | 11/2004 | Cumming |
| 2004/0243232 A1 | 12/2004 | Cumming |
| 2004/0249456 A1 | 12/2004 | Cumming |
| 2005/0021140 A1 | 1/2005 | Liao |
| 2005/0027354 A1 | 2/2005 | Brady et al. |
| 2005/0075732 A1 | 4/2005 | Israel |
| 2005/0096741 A1 | 5/2005 | Cumming |
| 2005/0107875 A1 | 5/2005 | Cumming |
| 2005/0125058 A1 | 6/2005 | Cumming et al. |
| 2005/0137703 A1 | 6/2005 | Chen |
| 2005/0267576 A1 | 12/2005 | Cumming |
| 2005/0288784 A1 | 12/2005 | Peyman |
| 2006/0064077 A1 | 3/2006 | Peyman |
| 2006/0064162 A1 | 3/2006 | Klima |
| 2006/0100704 A1 | 5/2006 | Blake et al. |
| 2006/0111776 A1 | 5/2006 | Glick et al. |
| 2006/0116764 A1 | 6/2006 | Simpson |
| 2006/0149369 A1 | 7/2006 | Cumming et al. |
| 2007/0021832 A1 | 1/2007 | Nordan |
| 2007/0032867 A1 | 2/2007 | Cumming |
| 2007/0129800 A1 | 6/2007 | Cumming |
| 2007/0129803 A1 | 6/2007 | Cumming et al. |
| 2007/0135915 A1 | 6/2007 | Klima |
| 2007/0142908 A1 | 6/2007 | Xu |
| 2007/0198084 A1 | 8/2007 | Cumming et al. |
| 2007/0244472 A1 | 10/2007 | Kuhn et al. |
| 2008/0027538 A1 | 1/2008 | Cumming |
| 2008/0027539 A1 | 1/2008 | Cumming |
| 2008/0027540 A1 | 1/2008 | Cumming |
| 2008/0046077 A1 | 2/2008 | Cumming |
| 2008/0086208 A1 | 4/2008 | Nordan |
| 2008/0154362 A1 | 6/2008 | Cumming |
| 2008/0281415 A1 | 11/2008 | Cumming |
| 2008/0281416 A1* | 11/2008 | Cumming .................. 623/6.37 |
| 2008/0288066 A1 | 11/2008 | Cumming |
| 2008/0294254 A1 | 11/2008 | Cumming et al. |
| 2008/0319545 A1 | 12/2008 | Cumming |
| 2009/0005866 A1 | 1/2009 | Cumming |
| 2009/0234449 A1 | 9/2009 | De Juan, Jr. et al. |
| 2009/0248154 A1 | 10/2009 | Dell |
| 2010/0004742 A1 | 1/2010 | Cumming |
| 2010/0057202 A1 | 3/2010 | Bogaert |
| 2011/0313519 A1 | 12/2011 | Cumming |
| 2011/0313524 A1 | 12/2011 | Cumming |
| 2011/0313525 A1 | 12/2011 | Cumming |
| 2011/0313526 A1* | 12/2011 | Cumming .................. 623/6.44 |
| 2012/0296424 A1 | 11/2012 | Betser |
| 2013/0073039 A1 | 3/2013 | Mirlay |
| 2013/0231742 A1 | 9/2013 | Deacon et al. |
| 2014/0088699 A1 | 3/2014 | Cumming |
| 2014/0155871 A1 | 6/2014 | Cumming |
| 2014/0172093 A1 | 6/2014 | Cumming |
| 2015/0012088 A1 | 1/2015 | Cumming |
| 2015/0073550 A1 | 3/2015 | Cumming |
| 2015/0088254 A1 | 3/2015 | Cumming |
| 2015/0182327 A1 | 7/2015 | Cumming |
| 2015/0182328 A1 | 7/2015 | Cumming |
| 2015/0245904 A1 | 9/2015 | Cumming |
| 2015/0245905 A1 | 9/2015 | Cumming |
| 2015/0272726 A1 | 10/2015 | Cumming |

FOREIGN PATENT DOCUMENTS

| | | |
|---|---|---|
| DE | 3626869 | 2/1988 |
| FR | 2728458 | 6/1996 |
| FR | 2728459 | 6/1996 |
| FR | 2734472 | 11/1996 |
| FR | 2765797 | 1/1999 |
| FR | 2991572 | 12/2013 |
| GB | 2171912 | 9/1986 |
| GB | 2226246 | 6/1990 |
| JP | 2003-190193 | 7/2003 |
| SU | 1123685 | 11/1984 |
| WO | WO 93/05733 | 4/1993 |
| WO | WO 01/19288 | 3/2001 |
| WO | WO 01/19289 | 3/2001 |
| WO | WO 03/017873 | 3/2003 |
| WO | WO 2007/037180 | 4/2007 |
| WO | WO 2009/048656 | 4/2009 |
| WO | WO 2009/086511 | 7/2009 |
| WO | WO 2011/151839 | 12/2011 |

OTHER PUBLICATIONS

Final Office Action for U.S. Appl. No. 13/092,359 dated Feb. 6, 2015 in 21 pages.
Final Office Action for U.S. Appl. No. 13/111,599 dated May 2, 2013 in 10 pages.
Final Office Action for U.S. Appl. No. 13/111,599 dated Feb. 6, 2015 in 21 pages.
Final Office Action for U.S. Appl. No. 13/155,327 dated Dec. 10, 2012 in 10 pages.
Final Office Action for U.S. Appl. No. 13/953,605 dated Sep. 25, 2014 in 17 pages.
International Search Report and Written Opinion for PCT/US13/61452 dated Feb. 24, 2014 in 11 pages.

(56) References Cited

OTHER PUBLICATIONS

International Search Report and Written Opinion for PCT/US2014/057037 dated Jan. 20, 2015 in 12 pages.
Office Action for U.S. Appl. No. 13/017,189 dated May 9, 2013 in 9 pages.
Office Action for U.S. Appl. No. 13/092,359 dated Oct. 25, 2012 in 10 pages.
Office Action for U.S. Appl. No. 13/092,359 dated Sep. 8, 2014 in 15 pages.
Office Action for U.S. Appl. No. 13/111,599 dated Jan. 2, 2013 in 11 pages.
Office Action for U.S. Appl. No. 13/111,599 dated Sep. 5, 2014 in 13 pages.
Office Action for U.S. Appl. No. 13/155,327 dated Jul. 20, 2012 in 7 pages.
Office Action for U.S. Appl. No. 13/155,327 dated Apr. 26, 2013 in 7 pages.
Office Action for U.S. Appl. No. 13/953,605 dated May 20, 2014 in 9 pages.
Office Action for U.S. Appl. No. 14/274,352 dated Feb. 12, 2015 in 10 pages.
Office Action for U.S. Appl. No. 13/891,088 dated Aug. 13, 2014 in 25 pages.
Office Action for U.S. Appl. No. 13/910,076 dated Nov. 7, 2014 in 12 pages.
Office Action for U.S. Appl. No. 14/143,162 dated Aug. 4, 2014 in 18 pages.
Office Action for U.S. Appl. No. 14/257,933 dated Oct. 31, 2014 in 9 pages.
Response to Office Action for U.S. Appl. No. 13/017,189 dated Aug. 8, 2013 in 5 pages.
Response to Final Office Action for U.S. Appl. No. 13/017,189 dated Dec. 18, 2014 in 10 pages.
Response to Office Action for U.S. Appl. No. 13/092,359 dated Jan. 31, 2013 in 8 pages.
Response to Final Office Action for U.S. Appl. No. 13/092,359 dated Jul. 29, 2013 in 7 pages.
Response to Final Office Action for U.S. Appl. No. 13/092,359 dated Jan. 8, 2015 in 9 pages.
Response to Office Action for U.S. Appl. No. 13/111,599 dated Apr. 9, 2013 in 6 pages.
Response to Office Action for U.S. Appl. No. 13/111,599 dated Jul. 30, 2013 in 6 pages.
Response to Office Action for U.S. Appl. No. 13/111,599 dated Jan. 6, 2015 in 13 pages.
Response to Office Action for U.S. Appl. No. 13/155,327 dated Oct. 26, 2012 in 5 pages.
Response to Office Action for U.S. Appl. No. 13/155,327 dated Apr. 10, 2013 in 5 pages.
Response to Office Action for U.S. Appl. No. 13/155,327 dated Jul. 25, 2013 in 5 pages.
Response to Office Action for U.S. Appl. No. 13/953,605 dated Aug. 19, 2014 in 7 pages.
Response to Final Office Action for U.S. Appl. No. 13/953,605 dated Dec. 18, 2014 in 12 pages.
Response to Office Action for U.S. Appl. No. 13/891,088 dated Dec. 15, 2014 in 8 pages.
Response to Office Action for U.S. Appl. No. 13/910,076 dated Feb. 9, 2015 in 10 pages.
Response to Office Action for U.S. Appl. No. 14/143,612 dated Jan. 5, 2015 in 8 pages.
Response to Office Action for U.S. Appl. No. 14/257,933 dated Feb. 2, 2015 in 10 pages.
Davison, J.A., Chapter 11: Intraocular Lenses, *Duane's Clinical Ophthalmology on CD-ROM*, Lippincott Willliams & Wilkins, 2005, vol. 6, pp. 1-46.
Final Office Action for U.S. Appl. No. 14/274,352 dated Jun. 8, 2015 in 27 pages.
Final Office Action for U.S. Appl. No. 13/891,088 dated Jul. 2, 2015 in 17 pages.
Final Office Action for U.S. Appl. No. 14/035,813 dated Sep. 30, 2015 in 26 pages.
Final Office Action for U.S. Appl. No. 14/143,612 dated Mar. 20, 2015 in 14 pages.
Final Office Action for U.S. Appl. No. 14/257,933 dated Mar. 19, 2015 in 23 pages.
First Action Interview Pre-Interview Communication for U.S. Appl. No. 14/741,230 dated Jul. 30, 2015 in 5 pages.
International Search Report and Written Opinion for PCT/US2014/072518 dated Jul. 23, 2015 in 15 pages.
Internet Archive Wayback Machine; Crystalens—Is Crystalens right for you?; downloaded from http://web.archive.org/web/20141025080709/http://crystalens.com/en-us/iscrystalensrightforyou.aspx (Archived Oct. 25, 2014; printed on Aug. 12, 2015).
Office Action for U.S. Appl. No. 13/092,359 dated Jun. 5, 2015 in 11 pages.
Office Action for U.S. Appl. No. 13/111,599 dated Jun. 26, 2015 in 12 pages.
Office Action for U.S. Appl. No. 14/270,166 dated Mar. 3, 2015 in 19 pages.
Office Action for U.S. Appl. No. 13/910,076 dated Apr. 10, 2015 in 26 pages.
Office Action for U.S. Appl. No. 14/035,813 dated Mar. 26, 2015 in 16 pages.
Office Action for U.S. Appl. No. 14/143,162 dated Jul. 27, 2015 in 13 pages.
Office Action for U.S. Appl. No. 14/257,933 dated Aug. 31, 2015 in 14 pages.
Response to Final Office Action for U.S. Appl. No. 13/092,359 dated May 6, 2015 in 9 pages.
Response to Office Action for U.S. Appl. No. 13/111,599 dated Jun. 8, 2015 in 12 pages.
Response to Office Action for U.S. Appl. No. 14/274,352 dated May 12, 2015 in 10 pages.
Response to Office Action for U.S. Appl. No. 13/910,076 dated Oct. 9, 2015 in 15 pages.
Response to Office Action for U.S. Appl. No. 14/035,813 dated Jul. 27, 2015 in 10 pages.
Response to Office Action for U.S. Appl. No. 14/143,612 dated Jul. 17, 2015 in 8 pages.
Response to Office Action for U.S. Appl. No. 14/257,933 dated Jul. 17, 2015 in 10 pages.
Final Office Action for U.S. Appl. No. 13/017,189 dated Oct. 28, 2015 in 9 pages.
Office Action for U.S. Appl. No. 14/712,827 dated Oct. 6, 2015 in 38 pages.
Office Action for U.S. Appl. No. 14/584,188 dated Oct. 6, 2015 in 21 pages.
Preliminary Amendment for U.S. Appl. No. 14/741,230 dated Oct. 14, 2015 in 12 pages.
Response to Final Office Action for U.S. Appl. No. 13/017,189, filed Apr. 13, 2015 in 8 pages.
Response to Office Action for U.S. Appl. No. 13/092,359, filed Oct. 26, 2015 in 14 pages.
Response to Office Action for U.S. Appl. No. 14/270,166, filed Aug. 3, 2015 in 12 pages.
Response to Office Action for U.S. Appl. No. 14/274,352, filed Oct. 22, 2015 in 14 pages.
Response to Office Action for U.S. Appl. No. 14/035,813, filed Oct. 20, 2015 in 13 pages.
Supplemental Response to Final Office Action for U.S. Appl. No. 13/017,189, filed Jun. 12, 2015 in 8 pages.

* cited by examiner

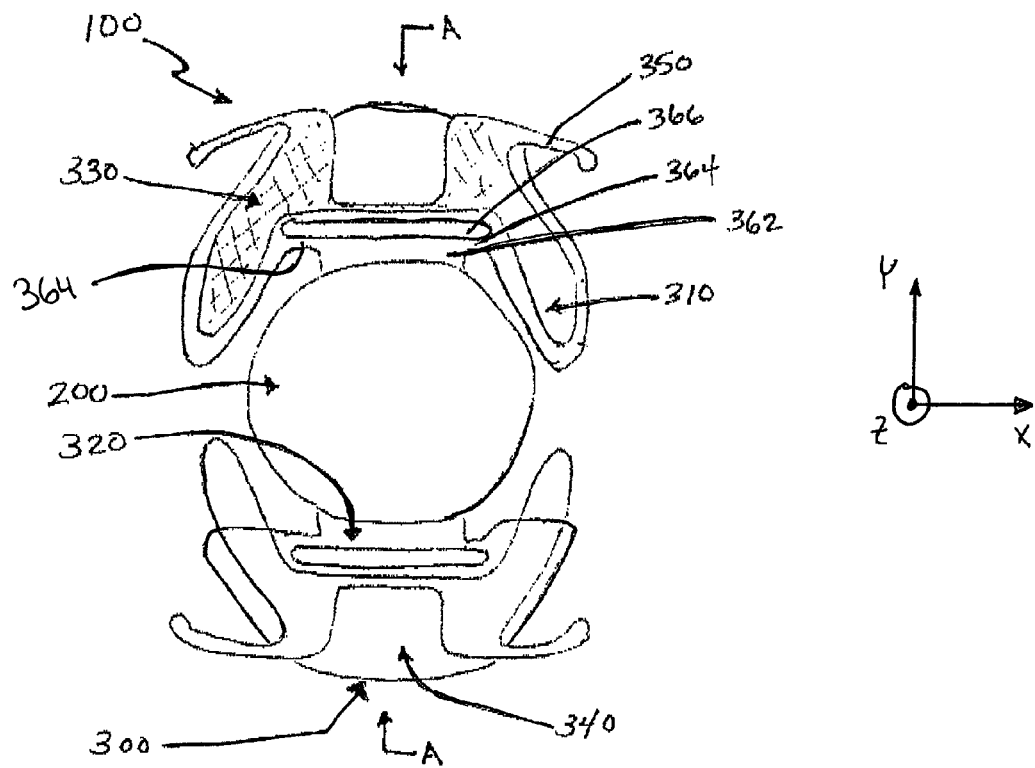
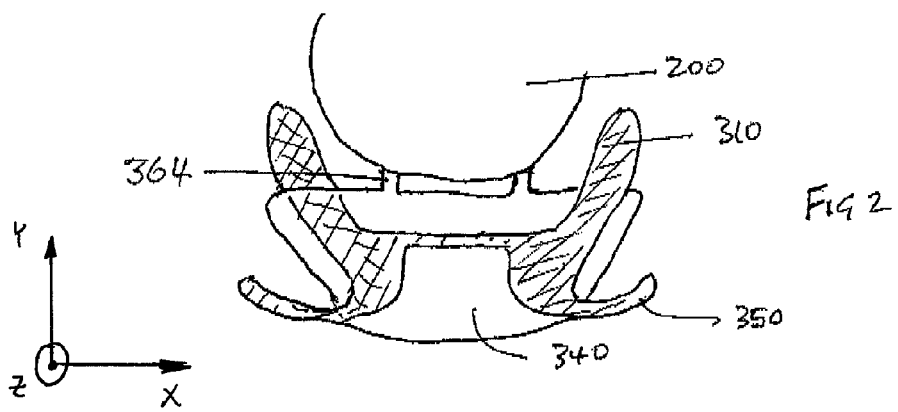

INTRAOCULAR LENS

This application is a continuation in part of U.S. patent application Ser. No. 13/910,076 titled Torsion Bar Accommodating Intraocular Lens which claims priority to U.S. Provisional Application No. 61/689,394, filed on Jun. 5, 2012. The contents and disclosures of each of these applications are fully incorporated herein by reference. This application also incorporated by reference the contents and disclosure of the following: U.S. Publication No. 20110313519, filed Jan. 31, 2011; U.S. Publication No. 2011/0313524, filed Apr. 22, 2011; U.S. Publication No. 2011/0313525, filed May 19, 2011; U.S. Publication No. 2011/0313526, filed Jun. 7, 2011; U.S. Pat. No. 8,523,942, filed May 15, 2012; U.S. Publication No. 2012/0310344, filed May 16, 2012; U.S. application Ser. No. 13/891,088, filed May 9, 2013; and U.S. application Ser. No. 13/910,076, filed Jun. 4, 2013.

BACKGROUND

1. Field

The present disclosure is related to a single focus intraocular lens, various embodiments of which provide seamless vision from distance to near.

2. Description of the Related Art

An intraocular lens (IOL) is a lens implanted into the eye, usually replacing a normal human lens that has been clouded over by a cataract, or can replace a normal human lens as a form of refractive surgery to change the eye's optical power.

Premium intraocular lenses (IOLs) implanted during cataract surgery are categorized three ways: accommodating, multifocal, and toric intraocular lenses.

The best visual acuity is achieved with the single focus accommodating lenses. The optic of these lenses moves forward and backward upon constriction and relaxation of the ciliary muscle. However, for reading in dim lighting conditions, or for small print, weak reading glasses are often necessary.

The multifocal lenses focus light on the retina at either two or three focal lengths. Thus, there is more than one image on the retina simultaneously. This creates problems since the amount of light in focus is divided between the multiple focal points, and contrast sensitivity is thereby reduced, making vision at all distances difficult in dim lighting. In addition, there are severe problems when driving at night when the pupil is dilated. Many patients experience severe glare and halos and many have had to have the multifocal lenses explanted and replaced with a single vision standard lens, because of this problem. However, the near vision with the multifocal lenses is superior to that of the current accommodating lens.

The toric lenses correct the eyes that have significant astigmatism.

The currently marketed plate accommodating intraocular lenses provide excellent distance and intermediate vision but sometimes can require weak, +1.00, reading glasses for prolonged reading, for seeing small print, or reading in dim lighting conditions.

Furthermore, it is important for intraocular lenses to have a consistent location along the axis of the eye to provide good uncorrected distance vision and to center in the middle of the vertical meridian of the eye. Without excellent uncorrected distance vision there is no point in implanting lenses designed to give seamless vision from far to near.

The original intraocular lens consisted of a single optic. These lenses frequently de-centered and dislocated and it was discovered that there was a need to center and fixate the lens optic in the vertical meridian of the eye.

Attachments to the optic that center and fixate the lens within the capsular bag are called haptics. Traditionally, haptics comprise multiple flexible loops of various designs, J loops, C loops, closed loops, and flexible radial arms. Recently, traditional haptics have been replaced in some lens designs with oblong, flat flexible plates, called plate haptics. These plate haptics usually made from silicone, are solid, flat, flexible and between 3.0 and 6.0 mm in width, 0.20 to 0.75 mm thick, and may have tapered, rounded or parallel sides. Plate haptics often have flexible loops or fingers that help center and fixate the lens within the capsular bag. These flexible fingers extend beyond the distal or outer end of the plate haptics and slightly beyond the diameter of the capsular bag and are designed to flex centrally to center and fixate the lens and its optic within the capsular bag.

An accommodating IOL (AIOL) permits refocusing of the eye by means of movement along the optical axis in response to the constriction or relaxation of ciliary muscles. Near vision results from a forward movement of the optic upon constriction of the ciliary muscle which increases the pressure in the posterior part of the eye with a simultaneous decrease in pressure in the anterior part of the eye. Distance vision results from the reverse pressure change that takes place upon relaxation of the ciliary muscle and the resultant backwards movement of the lens. The movement of the optic enables the patient implanted with the lens to automatically change their vision between far, intermediate and near.

AIOLs are known to include opposing haptics positioned on either side of a lens optic. Once a patient's cataract is removed, e.g. by phacoemulsification, the AIOL is placed into the empty capsular bag. The haptics help to center the AIOL and fixate it within the capsular bag by fibrosis. Such AIOLs are described in U.S. Pat. Nos. 5,674,282, 5,476,514, 5,496,366, to Cumming, herein incorporated by reference in its entirety.

Moreover, although current AIOLs provide patients with significantly restored distance and intermediate vision, adequate near vision is commonly lacking—often requiring that patients use weak reading glasses to enhance near vision.

SUMMARY

An accommodating intraocular lens according to an embodiment of the present disclosure is described that overcomes the deficiencies of present designs noted above.

In various embodiments, an accommodating intraocular lens comprises a lens optic coupled to at least one haptic and a torsion bar positioned between the lens optic and the at least one haptic such that the torsion bar facilitates accommodation by deforming in response to a vitreous pressure change.

The connecting portion unlike a flat hinge flexing mechanism or a flat thin stretching hinge may have a cross section that can be round, oval, square or any variation of these. The connecting portion can have a length of between about 0.1 to 1.5 mm, in various embodiments between about 0.5 and 1.0 mm, or between about 0.1 mm to 1.0 mm. The connecting portion can connect tangentially to the optic in a transverse direction across the lens body, or connect in a radial or perpendicular manner, to function by stretching, thinning, rotating, or any combination of these.

Certain aspects of this disclosure are directed toward an accommodating intraocular lens. The intraocular lens can include a lens optic having a diameter, at least one haptic coupled to the lens optic, and at least one connecting bar connecting the lens optic and the at least one haptic. The connecting bar can facilitate accommodation by deforming in response to a vitreous pressure change. The connecting bar can have a width and thickness less than 30% the diameter of the optic.

Certain aspects of this disclosure are directed toward an accommodating intraocular lens having a lens optic coupled to at least one haptic. The at least one haptic can be primarily disposed on opposite first and second sides of the lens optic. The first side, the lens optic, and the second side can be arranged along a longitudinal axis of the accommodating intraocular lens. The at least one connecting bar can connect the lens optic and the at least one haptic. The at least one connecting bar can have a length disposed substantially orthogonal to said longitudinal axis of said accommodating intraocular lens.

Certain aspects of this disclosure are directed toward an accommodating intraocular lens having a lens optic coupled to at least one haptic. The at least one haptic can be primarily disposed on opposite first and second sides of the lens optic. The first side, the lens optic, and the second side can be arranged along a longitudinal axis of the accommodating intraocular lens. The at least one connecting bar can connect the lens optic and the at least one haptic. The at least one connecting bar can have a length disposed substantially parallel to said longitudinal axis of said accommodating intraocular lens.

Certain aspects of this disclosure are directed toward an accommodating intraocular lens having a lens optic coupled to at least one haptic. The at least one haptic can be primarily disposed on opposite first and second sides of the lens optic. The first side, the lens optic, and the second side can be arranged along a longitudinal axis of the accommodating intraocular lens. The at least one connecting bar can connect the lens optic and the at least one haptic. The at least one connecting bar can have a length disposed at an angle within about 30 degrees (e.g., within about 10 degrees, about 15 degrees, within about 20 degrees, or about 25 degrees) from said longitudinal axis of said accommodating intraocular lens.

Certain aspects of this disclosure are directed toward an accommodating intraocular lens having a lens optic coupled to at least one haptic. The at least one haptic can be primarily disposed on opposite first and second sides of the lens optic. The first side, the lens optic, and the second side can be arranged along a longitudinal axis of the accommodating intraocular lens. The at least one connecting bar can connect the lens optic and the at least one haptic. The at least one connecting bar can have a length disposed at an angle within about 30 degrees (e.g., at least about 10 degrees, about 15 degrees, about 20 degrees, or about 25 degrees) from an axis orthogonal to said longitudinal axis of said accommodating intraocular lens (i.e., a transverse axis of said accommodating intraocular lens).

In any of the above mentioned aspects, the intraocular lens may further include an optic appendage attached to said lens optic. The connecting bar can connect the optic appendage and the at least one haptic. In other aspects, the connecting bar directly connects the optic to the at least one haptic.

In any of the above mentioned aspects, the connecting bar can have a length between about 0.1 and 2.0 mm.

In any of the above mentioned aspects, the connecting bar can have a circular cross-section orthogonal to the length of the bar. In other aspects, the connecting bar can have an ovular cross section orthogonal to the length of the bar. In yet other aspects, the connecting bar can have a square cross-section orthogonal to the length of the bar.

In any of the above mentioned aspects, the connecting bar can be configured to elongate when subjected to pressure changes. In certain aspects, the connecting bar can be configured to thin when subjected to pressure changes. In certain aspects, the connecting bar can be configured to rotate when subjected to pressure changes.

In any of the above mentioned aspects, the connecting bar can include the same material as the haptic. In other aspects, the connecting bar includes a different material than the haptic.

In any of the above mentioned aspects, the intraocular lens can include an elongate slot partially traversing the haptic in the transverse direction of said intraocular lens. In certain aspects, the slot can be between 0.1 to 0.5 mm in height and 2 to 5 mm in length. In certain aspects, the connecting bar can be configured to permit forward movement of the lens optic by stretching more than bending in response posterior pressure comparable to the vitreous pressure of an accommodating eye.

In any of the above mentioned aspects, the intraocular lens may not include a hinging feature between the lens optic and the haptic.

Other features and advantages of the present disclosure will become apparent from the following more detailed description, taken in conjunction with the accompanying drawings, which illustrate, by way of example, the principles of the presently described apparatus and method of its use.

BRIEF DESCRIPTION OF THE SEVERAL VIEWS OF THE DRAWING(S)

FIG. 1 illustrates a top plan view of an AIOL according to at least one embodiment of the present disclosure with transversely directed torsion bars connecting the optic to the haptics.

FIG. 2 illustrates a portion of an AIOL according to another embodiment of the present disclosure with generally longitudinally directed connector bars connecting the optic to the haptics.

DETAILED DESCRIPTION

The above-described drawing figures illustrate the described disclosure in at least one of its preferred embodiments, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present disclosure.

FIG. 1 illustrates accommodating intraocular lens (AIOL) 100 comprising an optic 200 a short appendage 362 attached to the optic and coupled to at least one haptic 300 as well as connection bars 364 connecting the optic to the at least one haptic via the appendage 362.

The AIOL 100 is placed into the capsular bag of a patient's eye during cataract surgery involving known techniques such as, for example, phacoemulsification. The lens is centered so that the optical axis of the lens coincides with that of the patient's eye. The haptics 300 contact the capsular bag and the natural fibrosis of the tissue secures the haptics 300, and consequently the AIOL 100, in place.

The optic 200 is preferably a single focus optic that gathers the incoming light and focuses it on the retina of the patient to affect vision. The optic 200 may be biconvex, refractive, diffractive, plano-convex, Fresnel, spheric, aspheric, toric, or of any other type that is preferably substantially single focus. In order to permit the optic 200 to be inserted into the eye through a small incision, the optic 200 is preferably made of a flexible optical material, such as, for example, silicone, acrylic, hydrogel, or other flexible optical material now known or hereafter developed.

The at least one haptic 300 comprises a first end 320 opposite a second end 340. The first end 320 of the haptic 300 can be proximal the optic 200 while the second end is distal to the optic. The first end 320 is flexibly coupled to a periphery of the optic 200 or short appendage 362. In at least one embodiment, the AIOL 100 comprises opposing haptics positioned linearly along a longitudinal axis A of the AIOL 100 (e.g., parallel to the y-axis).

The haptic body may be substantially flexible in the transverse direction (e.g., parallel to the x-axis) and substantially rigid in the longitudinal direction (e.g., parallel to the y-axis) to enable the AIOL 100 to be folded and inserted into the eye via a small incision. While the plate haptic is substantially rigid, the flexibility of the connecting bar may promote vaulting. In various embodiments, the haptic 300 is constructed of the same or similar flexible material as the optic, including, but not limited to: silicone, hydrogel, acrylic, or similar material.

The plate haptic 300 may comprise opposing lateral paddles 310. The paddles 310 and projecting fingers 350 operable to engage, fixate, and center the AIOL in the capsular bag. In certain aspects, the paddles 310 can include a different, more rigid material than the plate haptics 300. For example, the paddles 310 can be made of polyimide, prolene, or titanium. The paddles may be useful for dipping into the vitreous cavity to further increase the pressure. The paddles also help stabilize the lens to prevent the AIOL from tilting. The paddles can also prevent anterior dislocation of one of the two plate haptics. Such exemplary haptics 300 and paddles 310 are discussed in U.S. Patent Publication 2011-0313519 A1, published Dec. 22, 2011 (U.S. patent application Ser. No. 13/017,189); U.S. Patent Publication 2011-0313524 A1, published Dec. 22, 2011 (U.S. patent application Ser. No. 13/092,359); U.S. Patent Publication 2011-0313525 A1, published Dec. 22, 2011 (U.S. patent application Ser. No. 13/111,599); and U.S. Patent Publication 2011-0313526 A1, published Dec. 22, 2011 (U.S. patent application Ser. No. 13/155,327), incorporated herein by reference in their entireties.

The paddles 310 and/or the plate haptics 300 together can surround at least a portion of the optic or surround a majority of the optic. The paddles 310 and/or the plate haptics 300 together can surround between about 100 to 350 degrees of the optic, for example, between about 100 and 200 degrees, between about 150 degrees and 250 degrees, between about 200 degrees and about 300 degrees, or between about 250 degrees and 350 degrees. The paddles 310 together extend along the sides of the optic and more particularly about 50%, 60%, 70%, 80% or more of the length of the optic. In various embodiments, the paddles 310 extend along the optic 200 in the lateral direction (parallel to the x-axis) at least about 10% the diameter of the optic. In certain aspects, the paddles can include curved edges, for example, as shown in the figures, the paddles can curve inward to at least partially conform to the shape of the optic. In certain aspects, a length of the paddle can be at least two times, at least three times, or at least four times longer than a width of the paddle. In certain aspects, an end of the paddle closest to the optic can be tapered.

A frame 330 may be embedded within the haptic 300. The frame 330 may be formed of polyimide, prolene, polymethylmethanylate (PMMA), titanium, or similar material. The frame 330 may be a meshwork or lattice, designed and shaped in a manner to make the plate haptics rigid longitudinally but flexible transversely. Such exemplary frames 330 are discussed in U.S. Patent Publication 2011-0313519 A1, published Dec. 22, 2011 (U.S. patent application Ser. No. 13/017, 189); U.S. Patent Publication 2011-0313524 A1, published Dec. 22, 2011 (U.S. patent application Ser. No. 13/092,359); U.S. Patent Publication 2011-0313525 A1, published Dec. 22, 2011 (U.S. patent application Ser. No. 13/111,599); and U.S. Patent Publication 2011-0313526 A1, published Dec. 22, 2011 (U.S. patent application Ser. No. 13/155,327), incorporated herein by reference in their entireties.

The haptic 300 may further comprise projections 350, or fingers, extending from the second end (distal to the optic 200) to engage the capsular bag and secure and center the AIOL thereto. The projections 350 may be homogeneous with the frame and may be made of either polyimide, PMMA, acrylic or any other inert material. Such exemplary projections 350 are discussed in U.S. Patent Publication 2011-0313519 A1, published Dec. 22, 2011 (U.S. patent application Ser. No. 13/017,189); U.S. Patent Publication 2011-0313524 A1, published Dec. 22, 2011 (U.S. patent application Ser. No. 13/092,359); U.S. Patent Publication 2011-0313525 A1, published Dec. 22, 2011 (U.S. patent application Ser. No. 13/111,599); and U.S. Patent Publication 2011-0313526 A1, published Dec. 22, 2011 (U.S. patent application Ser. No. 13/155,327), incorporated herein by reference in their entireties.

The first end 320 of the haptic 300 (e.g., proximal to the optic 200) may be coupled to the optic or short appendage of the optic 362 via one or more connecting portions. The connecting bars 364 may operate to permit contraction of the ciliary muscles to cause an end-to-end compression of opposing haptics with an increase in vitreous pressure, with resultant movement of the optic being substantially forward. The connecting portions, bars, or members, 364 shown in FIG. 1 are capable of stretching, bending, and/or potentially rotating when subjected to posterior pressure. Depending on the configuration of the connecting portions 364, the connecting portions 364 may stretch along the length thereof, which may be at least in part along a direction substantially parallel to the longitudinal axis of the AIOL and/or may be at least partly along an axis that is substantially perpendicular to the longitudinal axis of the AIOL or along the transverse direction (e.g., parallel to x-axis and/or z-axis). Further, the connecting portions 364 may twist or rotate about an axis along the length of the connecting portion, which may be about an axis that is substantially perpendicular to the longitudinal axis of the AIOL (e.g. about an axis parallel to z-axis and/or x-axis) and/or may be about an axis that is substantially parallel to the longitudinal axis of the AIOL (e.g. about an axis parallel to y-axis) in some cases. In some embodiments, each of the connecting portions 364 can be positioned adjacent the optic periphery and flexibly coupled thereto. The connecting portions 364 can be oriented such that their length extends along an axis substantially parallel to a transverse axis of the AIOL 100 (e.g. along an axis parallel to the x-axis) as shown in FIG. 1 or substantially parallel to a longitudinal axis of the AIOL 100 as shown in FIG. 2.

With continued reference to FIG. 1, as disclosed above, one or more connecting portions 364 can be oriented along an axis substantially parallel to a transverse axis of the AIOL 100 (e.g. parallel to the x-axis). The AIOL 100 can include two connecting portions 364 for securing each haptic 300 to the short appendage 362 and optic 200. The connecting portions 364 can connect the haptic 300 to the short appendage 362 such that an elongate slot 366 is formed between the short appendage 362 and the haptic 300. An elongate axis of the elongate slot 366 can be substantially perpendicular to the longitudinal axis of the AIOL through line A-A (e.g. perpendicular to the y-axis) in some embodiments. Although not shown, the connecting portions 364 may be oriented along an axis that is less than or equal to about 5°, 10°, 15° 20°, 25°, 30°, 35°, 40°, or 45° from the transverse axis of the AIOL (e.g., axis parallel to x-axis).

The elongate slot 366 is an aperture formed in the haptic 300 that extends laterally and parallel to the transverse direction (e.g. parallel to the x-axis). Preferably, the slot 366 comprises an oval shape, but all shapes are specifically contemplated. As mentioned above, the slot 366 is adjacent the connecting portions distal to the optic 200. Preferably, the slot dimensions ranging from 0.1 to 0.5 mm in height and 2.0 to 5.0 mm in length.

As shown in FIG. 2, one or more connecting portions or connecting bar 364 can be oriented or extend along an axis that is substantially parallel to a longitudinal axis of the AIOL 100 (e.g. along an axis parallel to the y-axis). In some embodiments, the AIOL 100 can include two connecting portions or bars 364 for securing each haptic 300 to the optic 200 although more or less are possible. For example, although not shown, each haptic 300 can be connected to the optic 200 by a single connecting portion 364. Reducing the number of connecting portion 364 can be beneficial to decrease the force necessary to move the optic relative to the haptics. Although not shown, the connecting portions 364 may be oriented along an axis that is less than or equal to about 5°, 10°, 15° 20°, 25°, 30°, 35°, 40°, or 45° from the longitudinal axis of the AIOL (e.g., axis parallel to y-axis).

The connecting portions 364 can connect the haptic 300 to the optic 200 such that an elongate slot is formed between the optic 200 and the haptic 300. An elongate axis of the elongate slot can be substantially perpendicular to the longitudinal axis of the AIOL through line A-A (e.g. parallel to the x-axis).

The connecting portions 364 couples the optic 200 to the haptic 300 and is preferably of the same material as the optic. The connecting portions 364 assist in accommodation in that they decrease the resistance to the pressure that pushes the optic forward. In various embodiments, such connecting portions 364 are not hinges in the sense that they primarily stretch and do not bend like a hinge when the optic 200 is vaulted forward because of an increase in vitreous pressure during accommodation. Likewise, in various embodiments, the connecting portions 364 may not include a hinge feature, for example, between the optic 200 or appendage 362 and the haptic 300 about which portions of the connecting portion bend like a hinge. Example hinges or straps with hinge features are described in U.S. Patent Publication 2011-0313519 A1, published Dec. 22, 2011 (U.S. patent application Ser. No. 13/017,189); U.S. Patent Publication 2011-0313524 A1, published Dec. 22, 2011 (U.S. patent application Ser. No. 13/092, 359); U.S. Patent Publication 2011-0313525 A1, published Dec. 22, 2011 (U.S. patent application Ser. No. 13/111,599); and U.S. Patent Publication 2011-0313526 A1, published Dec. 22, 2011 (U.S. patent application Ser. No. 13/155,327), incorporated herein by reference in their entireties.

The connecting portions or bars 364 can extend lengthwise laterally (as in FIG. 1) or longitudinally (as in FIG. 2) between opposing paddles of the haptic along an axis either substantially parallel or substantially perpendicular to the longitudinal axis of the AIOL through line A-A. Moreover, the connecting portions are in various embodiments integral to the haptic 300 at each of the lateral ends (as shown in FIG. 1) or at each of the end distal to the optic 200 (as shown in FIG. 2), and are preferably of the same flexible material as the haptic. However, the connecting portions 364 may also be of a different material than the haptic 300, for example, such that the connecting portions are substantially more flexible than the haptic. In at least one embodiment, the connecting portions 364 may be from 0.1 to 1.5 mm in length. Preferably, the connecting portion 364 has a square or circular cross-section, but other cross-sectional solid shapes are specifically contemplated. Accordingly, in various embodiments, the cross-section has a width and height that are substantially equal and may be smaller than the length of the connecting portion or bar 364. For example, the width of the cross-section perpendicular to the length of the connecting portion or bar 364 may be less than 1.5, 1.4, 1.3, 1.2, or 1.0 times the height of the cross-section or may be smaller and possible larger in some embodiments. Similarly, the width of the cross-section perpendicular to the length of the connecting portion or bar 364 may be less than 2.0, 1.5, 1.2, or 1.0 times the length of connecting portion or bar or may be smaller and possible larger in some embodiments.

On insertion into the eye, the optic 200 and haptics 300 may be vaulted posteriorly. The haptics may move centrally and posteriorly in response to ciliary muscle contraction, i.e. end-to-end compression. Such movement increases the vitreous pressure, causing the optic to vault forward by stretching and potentially thinning of the connecting portion 364. This increase in pressure is further facilitated by the paddles dipping posteriorly into the vitreous cavity. This effect is facilitated by the stretching, and potentially thinning, bending, and/or rotation of the connecting portions in response to the increase in pressure. Relaxation of the ciliary muscle increases the diameter of the ciliary muscle and reduces the vitreous cavity pressure with a concomitant increase in pressure in the anterior part of the eye such that the optic 200 moves posteriorly to the distant vision position.

In at least one embodiment, the longitudinal length of the AIOL (e.g., from distal end to distal end, wherein the distal end is distal with respect to the optic 200) may be between approximately 9.0-11.0 mm, with the diameter as measured from the tips of the lateral finger projections with respect to the optic being between approximately 11.5-12.0 mm. The haptics 300 are in various embodiments between 3.0-6.0 mm wide and 0.20-0.75 mm thick, while the optic 200 may be approximately 5.0 mm in diameter and 1.0 mm thick at its center.

In various embodiments the connecting portions or connecting bars 364 are thin and experience more thinning when stretched. Without stretching, for example, the connecting portions or connecting bars 364 may be thin with respect to the optic 200 and the lens 100. In certain embodiments, for example as shown in FIG. 2, the connecting portion or connecting bar 364 may have a width in the transverse direction (e.g., parallel to the x-axis) less than 50%, 40%, 30%, 20%, 10%, 5% or less of the width or diameter of the optic 20. Similarly, the connecting portions or connecting bars 364 may have a thickness orthogonal to the transverse and longitudinal directions (e.g., parallel to the z-axis) that is less than 50%, 40%, 30%, 20%, 10%, 5% or less of the diameter of the width or diameter of the optic 20. The width and thicknesses may be greater than 0.5% or 1% of width or diameter of the optic 20 in some embodiments.

The dimensions described above allow for adequate stretching. Additionally, such widths may reduce the incidence of tearing when inserting the AIOL into the small opening made in the sclera or cornea of the eye. The AIOL is rolled to facilitate insertion and the resultant twisting can introduce shear forces on wider connections, which may cause tearing. Having narrow widths reduces the shear force and permits twisting without tearing.

The connecting portions or bars 364 such as shown in FIGS. 1 and 2 being thin permit stretching. In various embodiments, the connecting portions or bars 364 stretch and thereby increase their length by at least 0.5, 1.0, 1.5, or 2.0 times of their length or more. Accordingly, in some embodiments such as the configuration shown in FIG. 2 and possibly the configuration shown in FIG. 1, the connecting portions or bars 364 operate to permit vaulting forward of the optic during accommodation more by stretching than by bending. Likewise, in various embodiments, the connecting portions or bars 364 are configured to primarily stretch rather than bend (e.g., like a hinge) when the lens is exposed to posterior pressure akin to the increase pressure in the posterior part of the eye with an accommodating eye as well as a simultaneous anterior pressure akin to the simultaneous decrease in pressure in the anterior part of the eye during accommodation.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

The embodiments described in detail above are considered novel over the prior art of record and are considered critical to the operation of at least one aspect of the invention and to the achievement of the above-described objectives. The words used in this specification to describe the instant embodiments are to be understood not only in the sense of their commonly defined meanings, but to include by special definition in this specification: structure, material, or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense, it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and what incorporates the essential ideas.

The scope of this description is to be interpreted only in conjunction with the appended claims and it is made clear, here, that the named inventor believes that the claimed subject matter is what is intended to be patented.

What is claimed is:

1. An intraocular lens for improving vision, the intraocular lens configured for implantation in a capsular bag of an eye of a patient, the lens comprising:
   a single focus, optic comprising an optical material, the optic having a circular configuration configured to be centered about an optical axis of the eye when implanted, the lens having a longitudinal axis defining a length dimension of the lens and a transverse axis defining a width dimension of the lens, both of which are orthogonal to the optical axis of the eye when implanted, the transverse axis of the lens being perpendicular to the longitudinal axis of the lens, the optic having a first side and a second side, the first side of the optic and the second side of the optic being on opposite sides of the transverse axis of the lens;
   a pair of plate haptics, one of the plate haptics coupled to the first side of the optic and the other plate haptic coupled to the second side of the optic, the longitudinal axis of the lens extending through the optic and the pair of haptics, each plate haptic comprising:
      a proximal end and a distal end, the proximal end being closer to the optic than the distal end, each plate haptic comprising a haptic material; and
      a pair of opposing lateral paddles that are configured to stabilize the lens to prevent the intraocular lens from tilting, the pair of lateral paddles forming bilateral extensions of the haptic to at least partially surround the optic, the pair of lateral paddles configured to locate the optic in a posterior position along the optical axis of the eye when implanted;
   wherein a length dimension of the lateral paddles extends along more than 50% of a length of the optic, the length of the optic being measured along the longitudinal axis of the lens;
   wherein the pair of plate haptics, including the lateral paddles, surround between about 200 degrees and 350 degrees of a periphery of the optic; and
   wherein each plate haptic is flexibly coupled to the optic by a haptic connecting system comprising:
      a transverse appendage coupled to the optic, an elongate axis of the transverse appendage being substantially perpendicular to the longitudinal axis of the lens, a length of the transverse appendage measured along the elongate axis of the transverse appendage;
      a pair of connecting bars, one of the connecting bars being coupled to a first side of the transverse appendage and the other connecting bar being coupled to a second side of the transverse appendage, the first and second sides of the transverse appendage being on opposite sides of the longitudinal axis of the lens, each of the connecting bars extending transversely away from the transverse appendage, an elongate axis of each connecting bar being substantially perpendicular to the longitudinal axis of the lens, a length of each connecting bar measured along its respective elongate axis being shorter than the length of the transverse appendage, one of the connecting bars connecting one of the lateral paddles to the first side of the transverse appendage and the other connecting bar connecting the other lateral paddle to the second side of the transverse appendage; and a transverse slot extending completely through the haptic connecting system, an elongate axis of the slot being substantially perpendicular to the longitudinal axis of the lens;

wherein one of the transverse appendages is coupled to the first side of the optic and the other transverse appendage is coupled to the second side of the optic such that the longitudinal axis of the lens extends through two transverse appendages; and wherein each of the connecting bars is configured to stretch and twist upon an end-to-end compressive force from the capsular bag to cause the optic to be positioned posteriorly in the capsular bag upon implantation.

2. The intraocular lens of claim 1, wherein the optical material and the haptic material comprise the same material, and said material comprises acrylic.

3. The intraocular lens of claim 1, wherein the optical material comprises silicone.

4. The intraocular lens of claim 1, wherein the haptic material comprises silicone.

5. The intraocular lens of claim 1, wherein the haptic material comprises acrylic.

6. The intraocular lens of claim 1, wherein a length dimension of each lateral paddle is at least two times greater than a width dimension of the same paddle, the width dimension being measured perpendicular to the length dimension.

7. The intraocular lens of claim 6, wherein the length dimension of each lateral paddle is at least three times greater than the width dimension of the same paddle.

8. The intraocular lens of claim 6, wherein the length dimension of each lateral paddle is at least four times greater than the width dimension of the same paddle.

9. The intraocular lens of claim 1, wherein the pair of plate haptics and/or the lateral paddles surround between about 250 degrees and 350 degrees of the periphery of the optic.

10. The intraocular lens of claim 1, wherein the length dimension of the lateral paddles extends along more than 60% of the length of the optic.

11. The intraocular lens of claim 10, wherein the length dimension of the lateral paddles extends along more than 70% of the length of the optic.

12. The intraocular lens of claim 1, wherein a length of the slot is between 2.0 mm and 5.0 mm, the length of the slot being measured along its elongate axis.

13. The intraocular lens of claim 1, wherein the length of each of the connecting bars is between about 0.1 mm and 2.0 mm.

14. The intraocular lens of claim 1, wherein an inner edge of each of the lateral paddles is curved to at least partially conform to the circular configuration of the optic.

15. The intraocular lens of claim 1, wherein each of the connecting bars has a cross sectional shape perpendicular to its length which is circular.

16. The intraocular lens of claim 1, wherein each of the connecting bars has a cross sectional shape perpendicular to its length which is quadrilateral.

17. The intraocular lens of claim 1, wherein each plate haptic comprises a frame embedded within the haptic material, the frame comprising a different material that is more rigid than the haptic material to provide longitudinal rigidity to the haptic.

18. The intraocular lens of claim 17, wherein the more rigid material of the frame extends into each lateral paddle to provide longitudinal rigidity to the lateral paddles.

19. The intraocular lens of claim 17, wherein the more rigid material of the frame comprises polyimide or PMMA.

20. The intraocular lens of claim 17, wherein the frame is shaped to make its respective plate haptic more flexible about a longitudinal axis of the plate haptic than about a transverse axis of the plate haptic, the longitudinal axis of the plate haptic being perpendicular to the transverse axis of the plate haptic and collinear with the longitudinal axis of the lens, the transverse axis of the plate haptic being parallel to the transverse axis of the lens.

* * * * *